(12) United States Patent
Diede (10) Patent No.: US 6,477,474 B2
(45) Date of Patent: *Nov. 5, 2002

(54) MEASUREMENT OF PROCESS PRODUCT DIELECTRIC CONSTANT USING A LOW POWER RADAR LEVEL TRANSMITTER

(75) Inventor: Kurt C. Diede, Apple Valley, MN (US)

(73) Assignee: Rosemount Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/235,114

(22) Filed: Jan. 21, 1999

(65) Prior Publication Data

US 2002/0143500 A1 Oct. 3, 2002

(51) Int. Cl.$^7$ .................. G01R 27/04; G01R 27/26; G01N 22/00
(52) U.S. Cl. .................. 702/57; 702/79; 702/189; 702/65; 342/22; 73/290 R; 73/304 R; 324/637; 324/642; 324/644; 324/663
(58) Field of Search .............................. 702/57, 65, 79; 73/290 V, 304 R; 324/642, 643, 644, 637, 663; 342/22

(56) References Cited

U.S. PATENT DOCUMENTS 3,812,422 A * 5/1974 De Carolis ................. 324/58.5
3,832,900 A    9/1974 Ross ........................ 73/290 R (List continued on next page.)

FOREIGN PATENT DOCUMENTS

EP    0882956 A2    12/1998
EP    0882957 A2    12/1998

OTHER PUBLICATIONS

"Reflex–Radar Gauging and Level Measurement for Liquids, Interface and Granular Materials", Technical Data, 12/96.

Nozaki, R. et al., "Measurement of the Dielectric Properties of materials by Using Time Domain Reflectometry," 7$^{th}$ IEEE Instrumentation and Measurement Technology Conference Record, pp. 263–269 (1990).

Oswald, B. et al., "Determination of Volumetric Water Content in Lossy Geophysical Media Using Time Domain Reflectrometry," Antennas and Propagation Society International Symposium Digest, vol. 3, pp. 2054–2057 (1997).

Kramar, G.G et al., "Continuous Measurement of Cerebral Water Content by Time Domain Reflectometry," Proceedings of the Annual International Conference of the IEEE Engineering in Medicine and Biology Society, vol. 13, pp. 1593–1594 (1991).

*Primary Examiner*—Marc S. Hoff
*Assistant Examiner*—Paul Kim
(74) *Attorney, Agent, or Firm*—Westman, Champlin & Kelly, P.A.

(57) ABSTRACT

Disclosed is a method of using a low power radar level transmitter to calculate a dielectric constant of a product in a tank. Low Power Time Domain Reflectometry Radar (LPTDRR) circuitry is controlled to calculate a time delay between transmission of microwave energy down a termination extending into the product in the tank and reflection of the microwave energy. In some embodiments, the dielectric constant of the product is calculated as a function of the time delay. In other embodiments, the dielectric constant is calculated by controlling the LPTDRR circuitry to calculate amplitudes of transmit and receive pulses. The dielectric of the product is calculated as a function of the amplitudes of the transmit and receive pulses.

14 Claims, 11 Drawing Sheets

U.S. PATENT DOCUMENTS

| | | | | |
|---|---|---|---|---|
| 3,853,005 A | * | 12/1974 | Schendel | 73/290 R |
| 3,900,260 A | | 8/1975 | Wendt | 356/5 |
| 3,995,212 A | | 11/1976 | Ross | 324/58.5 B |
| 4,044,355 A | | 8/1977 | Edvardsson | 343/14 |
| 4,435,709 A | | 3/1984 | Kipp | 343/14 |
| 4,489,601 A | | 12/1984 | Rao et al. | 73/290 R |
| 4,786,587 A | * | 11/1988 | Mohr et al. | 324/58.5 |
| 4,838,690 A | | 6/1989 | Buckland et al. | 356/73.1 |
| 4,972,386 A | | 11/1990 | Lau | 367/99 |
| 5,157,337 A | | 10/1992 | Neel et al. | 324/632 |
| 5,313,168 A | * | 5/1994 | Ogawa | 324/663 |
| 5,345,183 A | * | 9/1994 | Take | 324/663 |
| 5,365,178 A | | 11/1994 | Van Der Pol | 324/644 |
| 5,440,310 A | | 8/1995 | Schreiner | 342/124 |
| 5,609,059 A | | 3/1997 | McEwan | 73/290 R |
| 5,610,611 A | | 3/1997 | McEwan | 342/89 |
| 5,656,774 A | | 8/1997 | Nelson et al. | 73/290 |
| 5,659,321 A | | 8/1997 | Burger et al. | 342/124 |
| 5,661,251 A | | 8/1997 | Cummings et al. | 73/866.5 |
| 5,726,578 A | | 3/1998 | Hook | 324/643 |
| 5,734,346 A | | 3/1998 | Richardson et al. | 342/124 |
| 5,811,677 A | * | 9/1998 | Cournanc | 73/304 R |
| 5,898,308 A | * | 4/1999 | Champion | 324/643 |
| 6,130,637 A | | 10/2000 | Meszaros et al. | 342/124 |
| 6,166,681 A | | 12/2000 | Meszaros et al. | 342/124 |
| 6,184,818 B1 | | 2/2001 | Meinel | 342/124 |
| 6,198,424 B1 | * | 3/2001 | Diede et al. | 342/22 |

\* cited by examiner

MEASUREMENT OF PROCESS PRODUCT DIELECTRIC CONSTANT USING A LOW POWER RADAR LEVEL TRANSMITTER

CROSS REFERENCE TO RELATED APPLICATIONS

This application is related to U.S. application Ser. No. 09/234,999, filed Jan. 21, 1999 entitled "MULTIPLE PROCESS PRODUCT INTERFACE DETECTION FOR A LOW POWER RADAR LEVEL TRANSMITTER".

BACKGROUND OF THE INVENTION

The process control industry employs process variable transmitters to remotely monitor process variables associated with substances such as solids, slurries, liquids, vapors, and gasses in chemical, pulp, petroleum, pharmaceutical, food and other food processing plants. Process variables include pressure, temperature, flow, level, turbidity, density, concentration, chemical composition and other properties. A process variable transmitter can provide an output related to the sensed process variable over a process control loop to a control room, such that the process can be monitored and controlled.

The process control loop can be a two-wire, 4–20 mA process control loop. With such a process control loop, the energization levels are low enough that even under fault conditions the loop generally will not contain enough electrical energy to generate a spark. This is particularly advantageous in flammable environments. Process variable transmitters can sometimes operate on such low energy levels that they can receive all electrical power from the 4–20 mA loop. The control loop may also have digital signals superimposed on the two-wire loop according to a process industry standard protocol such as the HART® digital protocol.

Low power Time Domain Reflectometry radar (LPTDRR) instruments have been used to measure the level of process products (either liquids or solids) in storage vessels. In Time Domain Reflectometry, electromagnetic energy is transmitted from a source, and reflected at a discontinuity. The travel time of the received pulse is based on the media through which it travels. One type of LPTDRR is known as Micropower Impulse Radar (MIR), which was developed by Lawrence Livermore National Laboratory. Since LPTDRR level transmitters typically determine level as a function of the time of travel of microwave signals to and from an interface or surface of the product, and since time of travel is dependent upon the dielectric constant of material through which the microwaves travel, it can be necessary to know the dielectric constant(s) ahead of time. This is particularly necessary when the storage tank contains multiple products layered on top of one another, thus creating multiple interfaces between products having different dielectric constants. Prior LPTDRR level transmitters have required that an operator of the transmitter enter a dielectric constant of the product in order to determine the level of the multiple interfaces. A method of determining the dielectric constant(s) of one or more products in a tank would be a significant improvement in the art.

SUMMARY OF THE INVENTION

Disclosed is a method and level transmitter which calculate a dielectric constant of a product in a tank. Low Power Time Domain Reflectometry Radar (LPTDRR) circuitry is controlled to calculate a time delay between transmission of microwave energy along a termination extending into the product in the tank and reflection of the microwave energy. In some embodiments, the dielectric constant of the product is calculated as a function of the time delay. In other embodiments, the dielectric constant is calculated by controlling the LPTDRR circuitry to calculate amplitudes of transmit and receive pulses. The dielectric of the product is calculated as a function of the amplitudes of the transmit and receive pulses.

DETAILED DESCRIPTION OF THE PREFERRED EMBODIMENTS

Figure 1:
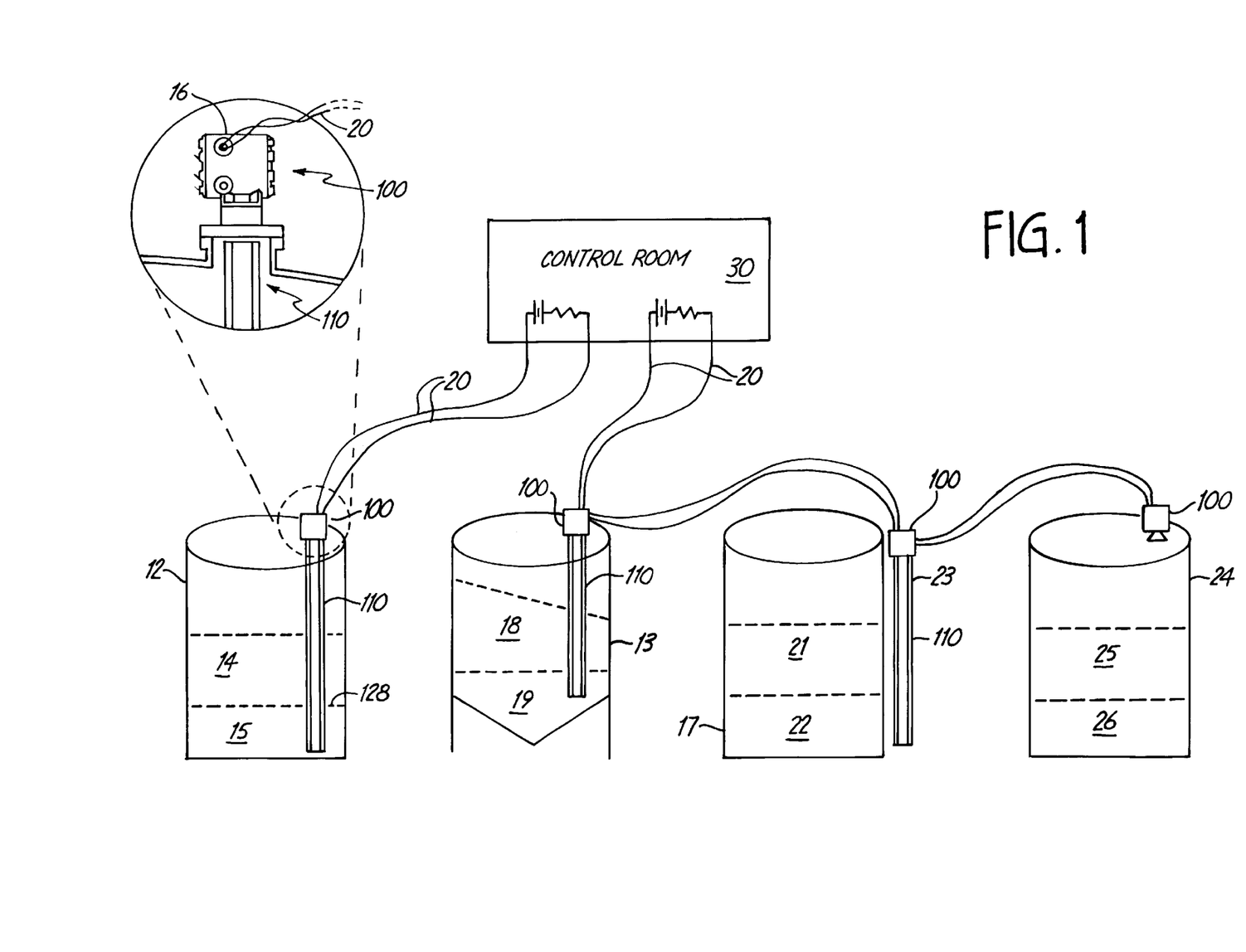
FIG. 1 is a diagram of a process control system illustrating the environment of embodiments of the invention.

FIG. 1 is a diagram illustrating level transmitters 100 operating in the environment of being mounted to storage tanks 12, 13, 17, 24 containing at least one product. As illustrated, tank 12 contains first product 14 positioned on top of second product 15. Transmitters 100 include housings 16 and terminations 110. Transmitters 100 are coupled to process control loops 20, and transmit information related to dielectric constants and/or heights of the process products over loops 20 to control room 30 (which is modelled as voltage sources and resistances) or to other devices (not shown) coupled to process control loops 20. Loops 20 are sources of power for transmitters 100 and can use any process industry standard communications protocol such as 4–20 mA, Foundation™ Fieldbus, or HART®. As low power radar transmitters, transmitters 100 can be completely powered by energy received over a 4–20 mA process control loop.

FIG. 1 illustrates various applications in which radar dielectric constant measurement is useful. For example, process products 14 and 15 in tank 12 are fluids, while process products 18 (shown having a given angle of repose) and 19 in tank 13 are solids. Process products 21 and 22 in tank 17 are fluids the levels of which are communicated to tube 23 into which one of terminations 110 extends. Further, tank 24 is shown containing products 25 and 26, and having a radiative-type termination mounted on top of tank 24. Although tanks 12, 13, 17 and 24 are shown in FIG. 1, the embodiments of the invention may be practiced without tanks such as in a lake or reservoir.

Figure 2:
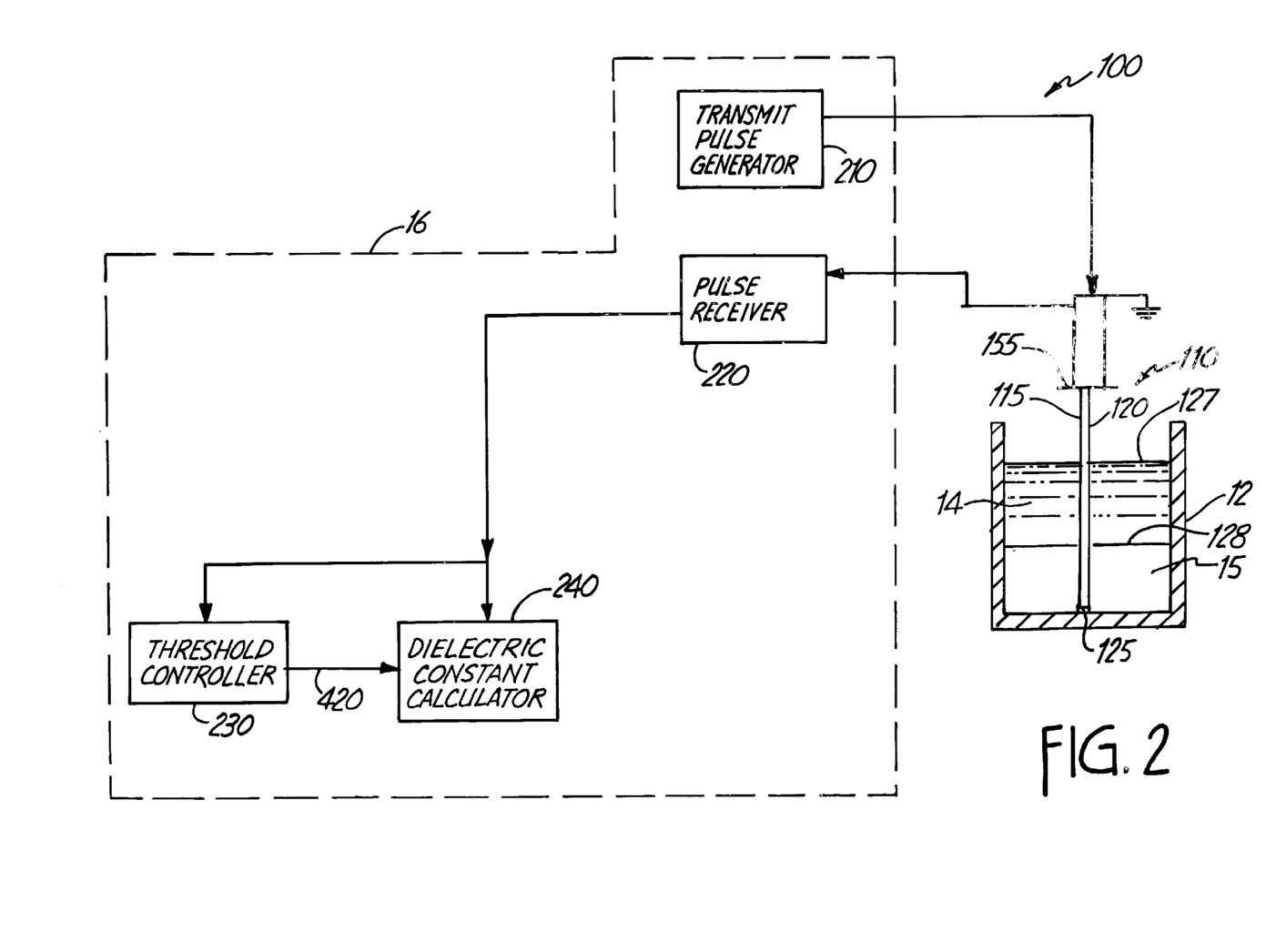
FIG. 2 is a block diagram illustrating circuitry of a radar level transmitter in accordance with an embodiment of the invention.
Figure 3:
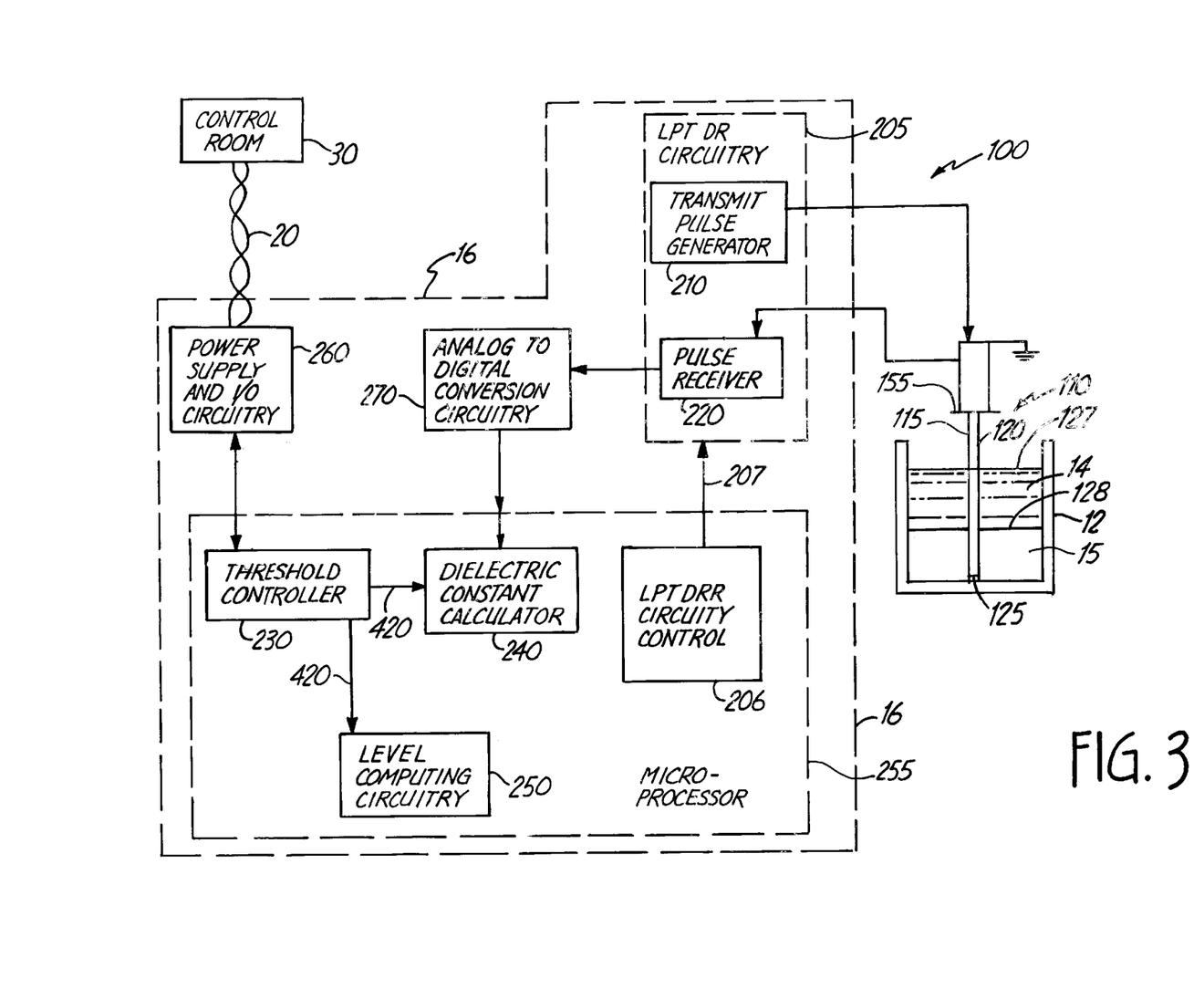
FIGS. 3 is a block diagram illustrating circuitry of a radar level transmitter in accordance with an alternate embodiment of the invention.
Figure 4:
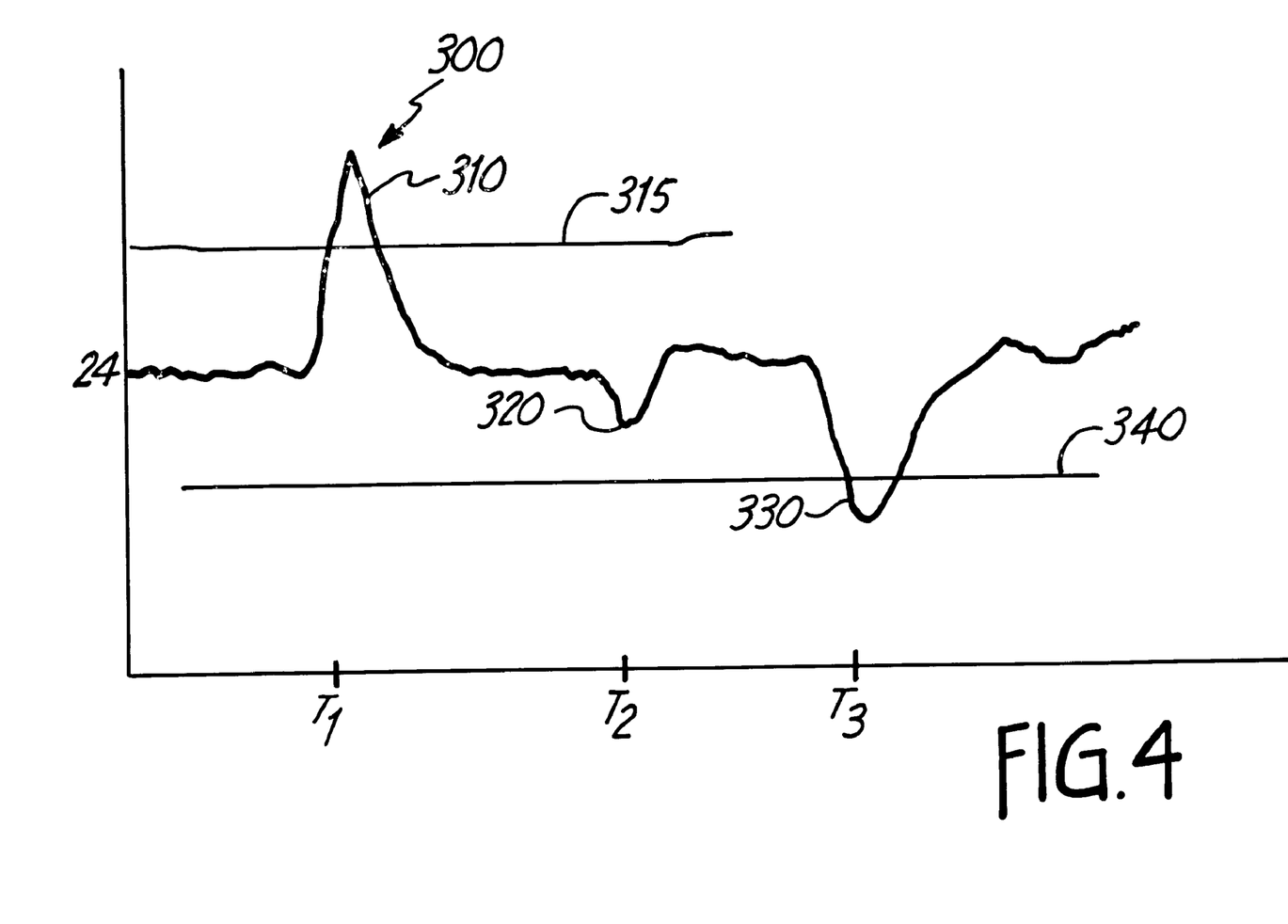
FIGS. 4 and 5 are plots illustrating Low Power Time Domain Reflectometry (LPTDRR) equivalent time waveform controllable thresholds.
Figure 5:
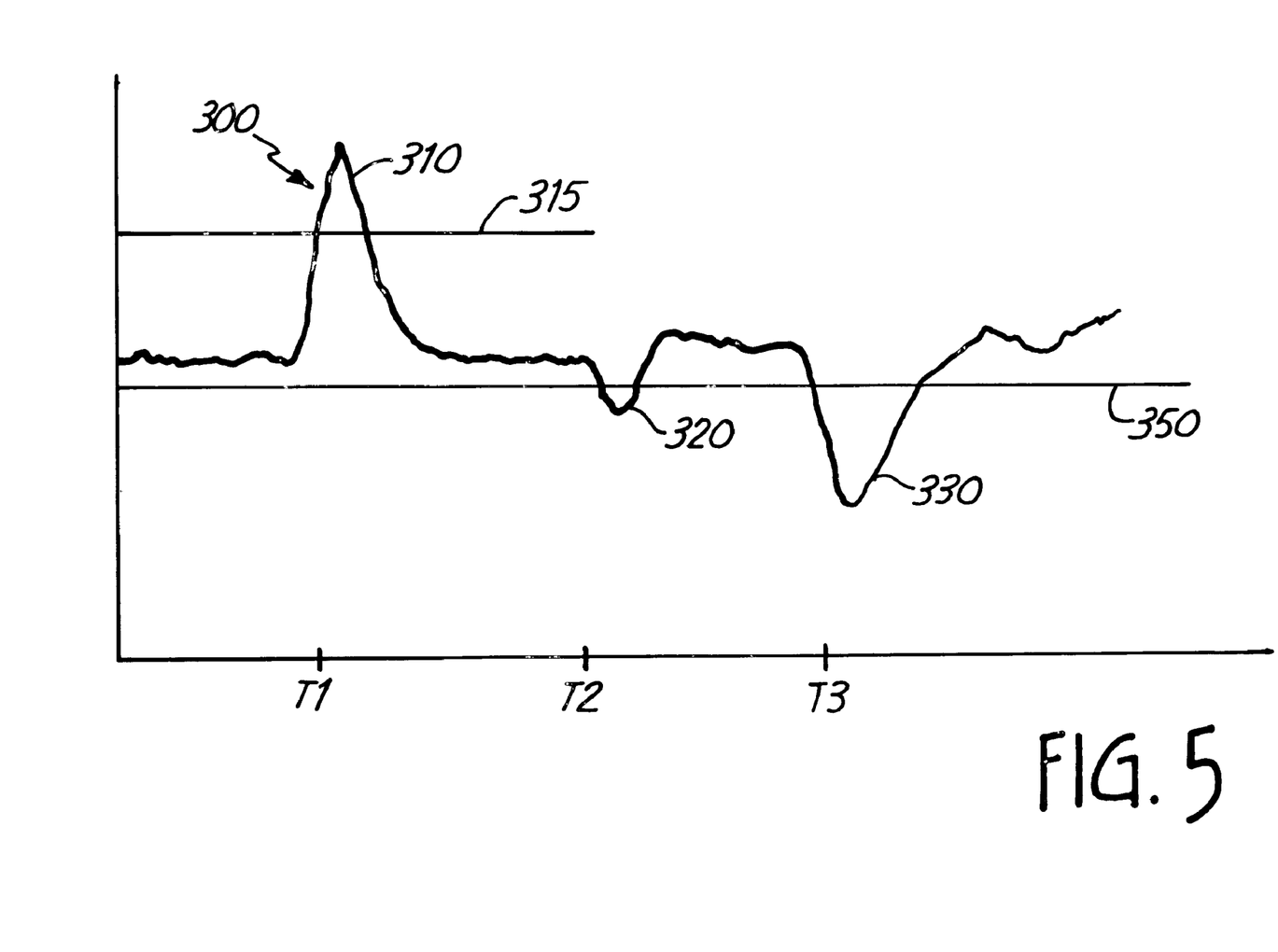

FIGS. 2 and 3 are block diagrams of a transmitter 100. FIGS. 4 and 5 are plots of equivalent time Low Power Time Domain Reflectometry Radar (LPTDRR) transmit/receive waveforms illustrating controllable threshold detector aspects of the invention. Within housing 16, transmitter 100 includes LPTDRR circuitry 205 (shown in FIG. 3), LPT-DRR circuitry controller 206 (shown in FIG. 3) and dielectric constant calculator 240. Controller 206 controls LPT-DRR circuitry 205 via connections 207 in order to determine a parameter which is proportional to the dielectric constant of product 14 in tank 12. Dielectric constant calculator 240 calculates the dielectric constant of product 14 as a function of the determined parameter. LPTDRR circuitry 205 can include transmit pulse generator 210 and pulse receiver 220.

Transmitter 100 also includes threshold controller 230 and optionally level computing circuitry 250 (shown in FIG. 3). Threshold controller 230 can be a component of LPTDRR circuitry 205. Threshold controller 230, dielectric constant calculator 240, level computing circuitry 250 and LPTDRR controller 206 can be implemented in microprocessor 255 as shown in FIG. 3. However, discrete circuitry for any of these functions can be used. In embodiments in which these functions are embodied in microprocessor 255, transmitter 100 includes analog-to-digital converter 270. Transmitter 100 can also include power supply and input/output circuitry 260 (as shown in FIG. 3) for powering transmitter 100 with power received over loop 20, and for communicating over loop 20. Such communication can include transmitting information related to the process product over loop 20. The power supply circuitry can be adapted to provide the sole source of power for transmitter 100 from power received over loop 20.

Microwave termination 110 can be of the type which are well known in the level transmitter art and can be any appropriate transmission line, waveguide or antenna. A transmission line is a system of material boundaries forming a continuous path from one place to another and capable of directing transmission of electromagnetic energy along this path. In some embodiments, termination 110 is a twin lead antenna having leads or conductors 115 and 120 connected at bottom region 125 and extendable into products 14 and 15 in tank 12, and optionally having launch plate 155. Termination 110 can also be a monopole, coaxial, twin-line, single-line, microstrip, or radiative horn termination and can have any appropriate number of leads.

Transmit pulse generator 210 is preferably a low power microwave source coupled to termination 110. Under the control of controller 206, generator 210 generates a microwave transmit pulse or signal which is transmitted along termination 110 into products 14, 15. The transmit pulse can be at any of a wide range of frequencies, for example between about 250 MHz and about 20 GHz or more. In one embodiment the frequency of the transmit pulse is about 2.0 GHz. Fiducial pulse 310 of equivalent time waveform 300 (shown in FIGS. 4 and 5) can be created at launch plate 155 or by other mechanisms to designate the beginning of a transmit/receive cycle. A first portion of the transmit pulse microwave energy transmitted along leads 115 and 120 is reflected at first product interface 127 between air and product 14. A second portion of the transmit pulse microwave energy is reflected at interface 128 between product 14 and product 15. If tank 12 contains only product 14, but not product 15, interface 128 is typically the bottom of the termination or tank. In FIGS. 4 and 5, pulse 320 of equivalent time waveform 300 represents microwave energy reflected at interface 127 between air and product 14, while pulse 330 represents microwave energy reflected at interface 128. Those skilled in the art will recognize that the waveforms shown in FIGS. 4 and 5 can be inverted without departing from the spirit and scope of the invention. In general, if product 14 has a dielectric constant which is less than the dielectric constant of product 15, the amplitude of pulse 330 should be larger than pulse 320.

Pulse receiver 220 is a low power microwave receiver coupled to termination 110. Receiver 220 receives the first reflected wave pulse corresponding to reflection of the first portion of the transmit pulse at the first product interface 127 (represented by pulse 320 in FIGS. 4 and 5). Receiver 220 also receives the second reflected wave pulse corresponding to reflection of the second portion of the transmit pulse at the second product interface 128 (represented by pulse 330 in FIGS. 4 and 5). Using a known low power time domain reflectometry radar sampling technique, pulse receiver 220 produces as an output equivalent time LPTDRR waveform 300.

Threshold controller 230 receives waveform 300 as an input. In embodiments in which threshold controller 230 and dielectric constant calculator 240 are embodied in microprocessor 255, analog-to-digital circuitry 270 digitizes waveform 300. Threshold controller 230 generates thresholds 315, 340 and 350 for detection of fiducial pulse 310 and thus time $T_1$ at which pulse 310 was received, detection of reflected wave pulse 320 and thus time $T_2$ at which pulse 320 was received, and detection of reflected wave pulse 330 and thus time $T_3$ at which pulse 330 was received. Threshold value 315 used to detect fiducial pulse 310 can be a predetermined constant voltage, or can be automatically determined as a function of the peak amplitude of pulse 310 in a known manner. Threshold controller 230 provides receive pulse threshold 340 shown in FIG. 4 at a level which is surpassed by pulse 330. Threshold controller 230 provides receive pulse threshold 350 shown in FIG. 5 at a level which is surpassed by pulse 320. Threshold controller 230 provides as an output to dielectric constant calculator 240 and to circuitry 250, receive pulse output information based upon detection of reflected wave pulses 320 and/or 330.

Figure 6:
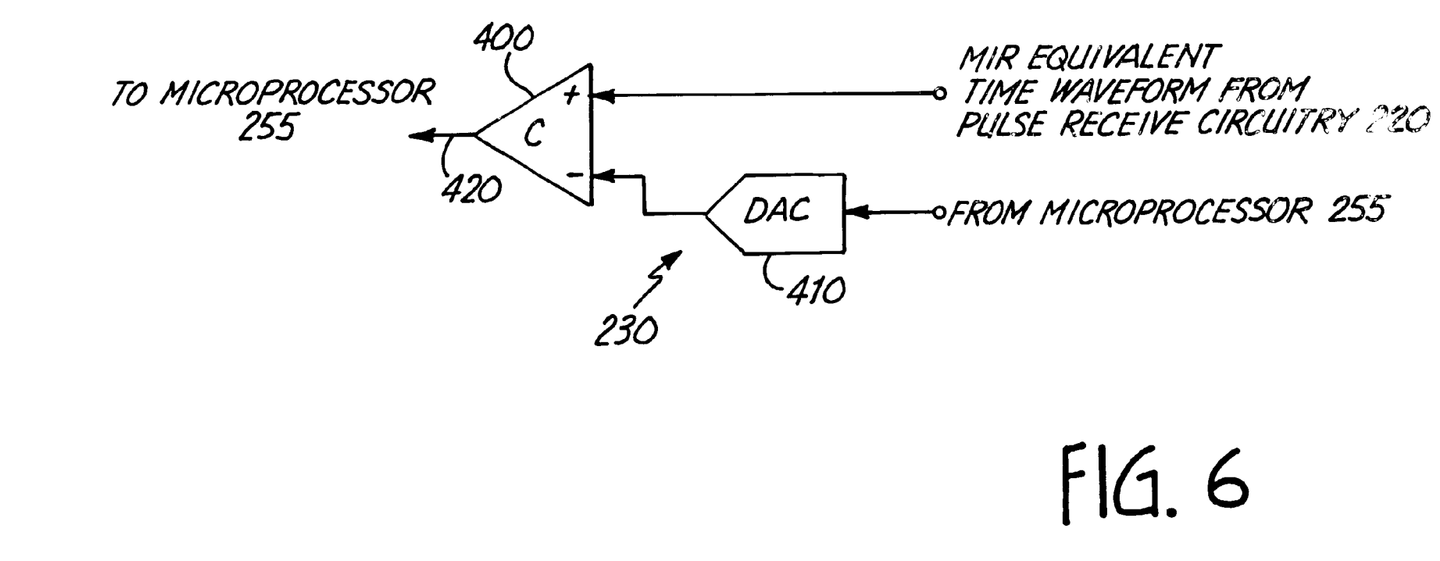
FIG. 6 is a schematic diagram of a controllable receive threshold circuitry in accordance with an embodiment of the invention.

FIG. 6 illustrates a portion of threshold controller 230, implemented in discrete circuitry, which generates controllable thresholds such as thresholds 340 and 350. Threshold controller 230 includes comparator 400, having a first input from receiver 220 waveform 300 containing receive pulses 320 and 330. As a second input, comparator 400 receives the controllable analog threshold voltage which is provided from the output of digital-to-analog converter 410. Converter 410 receives a digital input from microprocessor 255 representative of the desired threshold. The output 420 of comparator 400 is provided to dielectric constant calculator 240 and level computing circuitry 250 as an indication of the times that pulses 320 and 330 are received. During a first scan cycle in which waveform 300 is generated, converter 410 is controlled to provide threshold 350 for detection of pulse 320. During a subsequent scan cycle, converter 410 is controlled to provide threshold 340 for detection of pulse 330. The thresholds can be used to detect the times of receipt of the reflected wave pulses. The thresholds can also be controlled to determine the amplitudes of the reflected wave pulses.

Dielectric constant calculator 240 in FIG. 2 is coupled to threshold controller 230 and is adapted to calculate a dielectric constant of first product 14 in tank 12 as a function of the receive pulse output information provided by threshold controller 230. Methods implemented by circuitry 240 in calculating the dielectric constant are discussed below in detail with reference to FIGS. 7–12.

The relationship between the distance travelled by a microwave signal and the time of travel is shown in Equation 1.

$$D = \left(\frac{1}{\sqrt{\varepsilon_R}}\right) C\left(\frac{T}{2}\right) \qquad \text{Eq. 1}$$

where:

- $T/2$ = one half of the travel time of the microwave pulse to and from the interface;
- $\varepsilon_R$ = the dielectric constant of the material through which the microwave pulse travels (for air, $\varepsilon_R = 1$);
- $C$ = the speed of light; and
- $D$ = the distance traveled from the top of the termination to the interface.

Using this relationship, the dielectric constant of a material being measured can be calculated. The time of travel of a microwave is dependant upon the dielectric constant of the medium it is travelling through. The dielectric constant of the medium is proportional to the travel time according to the relationship shown in Equation 2.

$$\varepsilon_R \propto (A \cdot \text{Time})^2 \qquad \text{Eq. 2}$$

where:

- Time = microwave travel time through medium; and
- $A$ = a proportionality constant.

Also, the amplitude of the pulse reflected off of an interface with a material is proportional to the dielectric constant of the material according to the relationship shown in Equation 3.
where:

$V_R$ = the amplitude of the reflected pulse; and $$\varepsilon_R \propto \frac{V_R}{V_T} \qquad \text{Eq. 3}$$

$V_T$ = the amplitude of the transmitted pulse.

Using the relationships illustrated in Equations 2 and 3, independently or in combination, the dielectric constant (s) of one or more products or materials in a tank can be calculated.

METHODS

Figure 7:
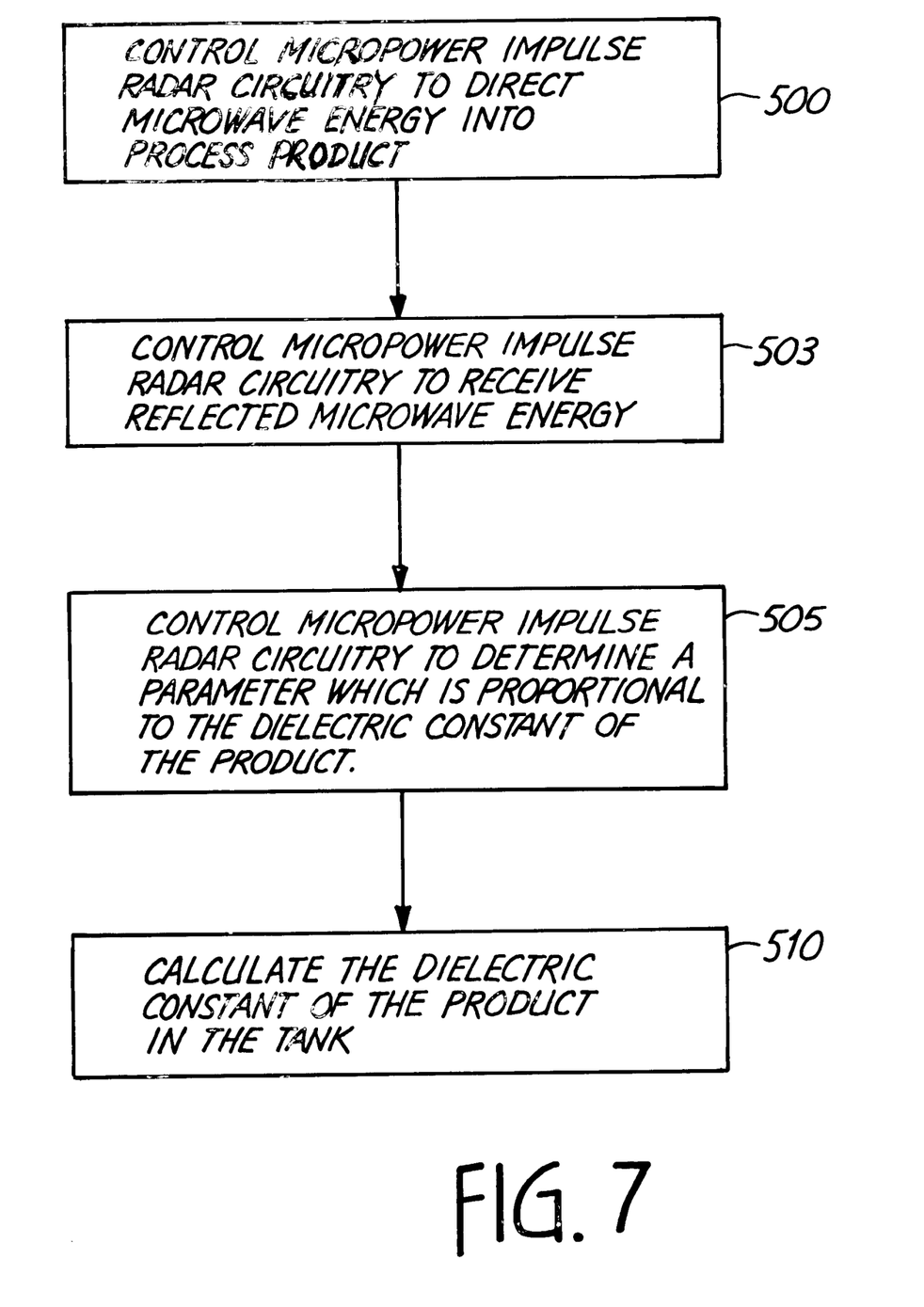
FIGS. 7, 9 and 12 are flow diagrams illustrating methods implemented by the microwave transmitter of FIG. 2.

A method of calculating the dielectric constant of product 14 is illustrated in FIG. 7. The method begins at block 500 with controlling the low power time domain reflectometry radar (LPTDRR) to direct microwave energy into the process product. At block 503, the LPTDRR circuitry is controlled to receive the reflected microwave energy. At block 505 the LPTDRR circuitry is controlled to measure a parameter which is proportional to the dielectric constant of product 14. Then, at block 510, the dielectric constant of product 14 is calculated as a function of the measured parameter using the relationships of Equation 2 and/or Equation 3.

Figure 8:
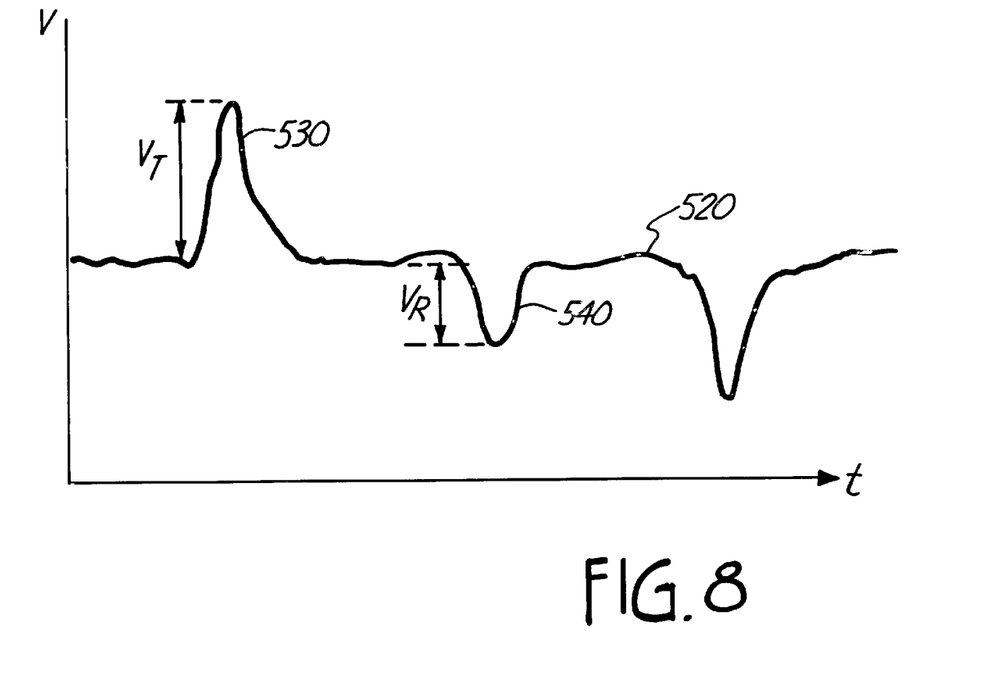
FIGS. 8, 10 and 11 are plots illustrating LPTDRR equivalent time waveforms.

A first more particular method of calculating the dielectric constant of product 14 with the relationship of Equation 3 uses threshold controller 230 to more precisely measure the transmitted and reflected pulse amplitudes. The method is shown in the plot of FIG. 8, and is summarized in the flow diagram of FIG. 9. Those skilled in the art will recognize that the waveform shown in FIG. 8 can be inverted without departing from the spirit and scope of the invention.

Figure 9:
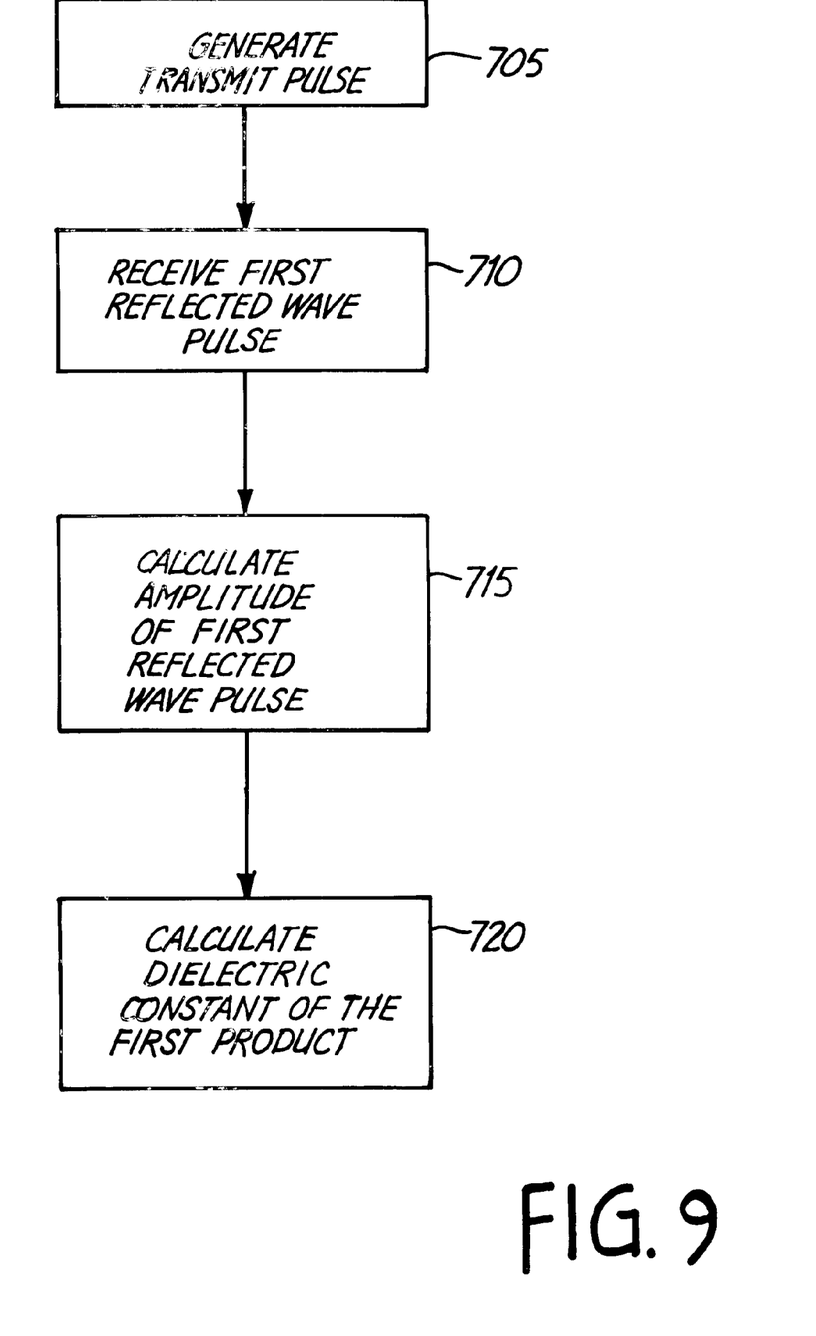

The method begins at block 705 with generating a transmit pulse. The transmit pulse is transmitted along the termination into the products in the tank, and reflects off of surfaces 127 and 128. At block 710, the first reflected wave pulse 540 is received. The first reflected wave pulse corresponds to reflection of the first portion of the transmit pulse at the first product interface 127. After controlling LPTDRR circuitry 205 to receive the reflected wave pulse, at block 715 the amplitude of the first reflected wave pulse is calculated. The amplitude of the first reflected wave pulse is a parameter which is proportional to the dielectric constant of product 14.

At block 720, the dielectric constant of the first product is calculated as a function of the first reflected wave pulse. As shown in equivalent time LPTDRR waveform 520 of FIG. 8, the transmit pulse (represented by fiducial pulse 530) has a transmit amplitude $V_T$, while the receive pulse 540 has a receive amplitude $V_R$. Either by digitizing the equivalent time LPTDRR waveform 520 with analog-to-digital converter 270 and analyzing the digitized signal with microprocessor 255, or by using digital-to analog converter 410 to set comparator thresholds, the amplitude of the first reflected wave pulse is calculated, and the dielectric constant of first product 14 is calculated using Equation 3. Thus, the calculated parameter which is proportional to the dielectric constant of product 14 is typically a ratio between the amplitude of the first reflected wave pulse and the amplitude of the transmitted pulse. Controlling the LPTDRR circuitry includes controlling threshold controller 230 to adjust a threshold to calculate the amplitude of reflected wave pulse 540.

Figure 10:
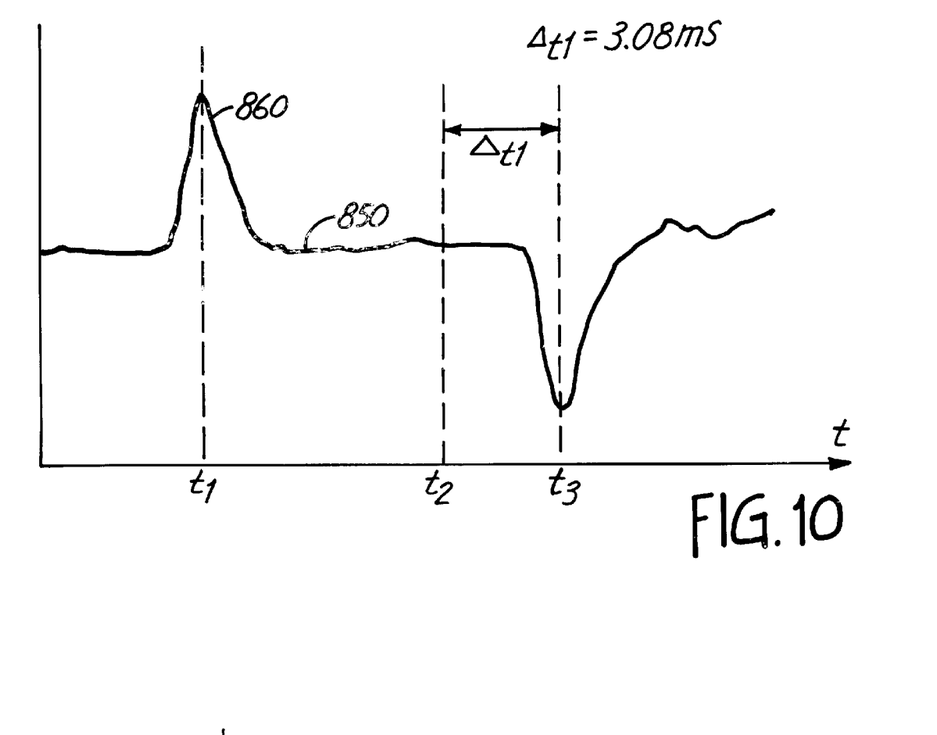

A second more particular method of calculating the dielectric constant of product 14, with the relationship of Equation 2, uses threshold controller 230 to calculate a time delay between transmission of the transmit pulse and reflection of the pulse from surface 128. More particularly, the method calculates a time of travel of the microwaves through a known distance of product 14. The method is shown in the plots of FIGS. 10 and. 11 and is summarized in the flow diagram of FIG. 12. Those skilled in the art will recognize that the waveforms shown in FIGS. 10 and 11 can be inverted without departing from the spirit and scope of the invention.

Figure 12:
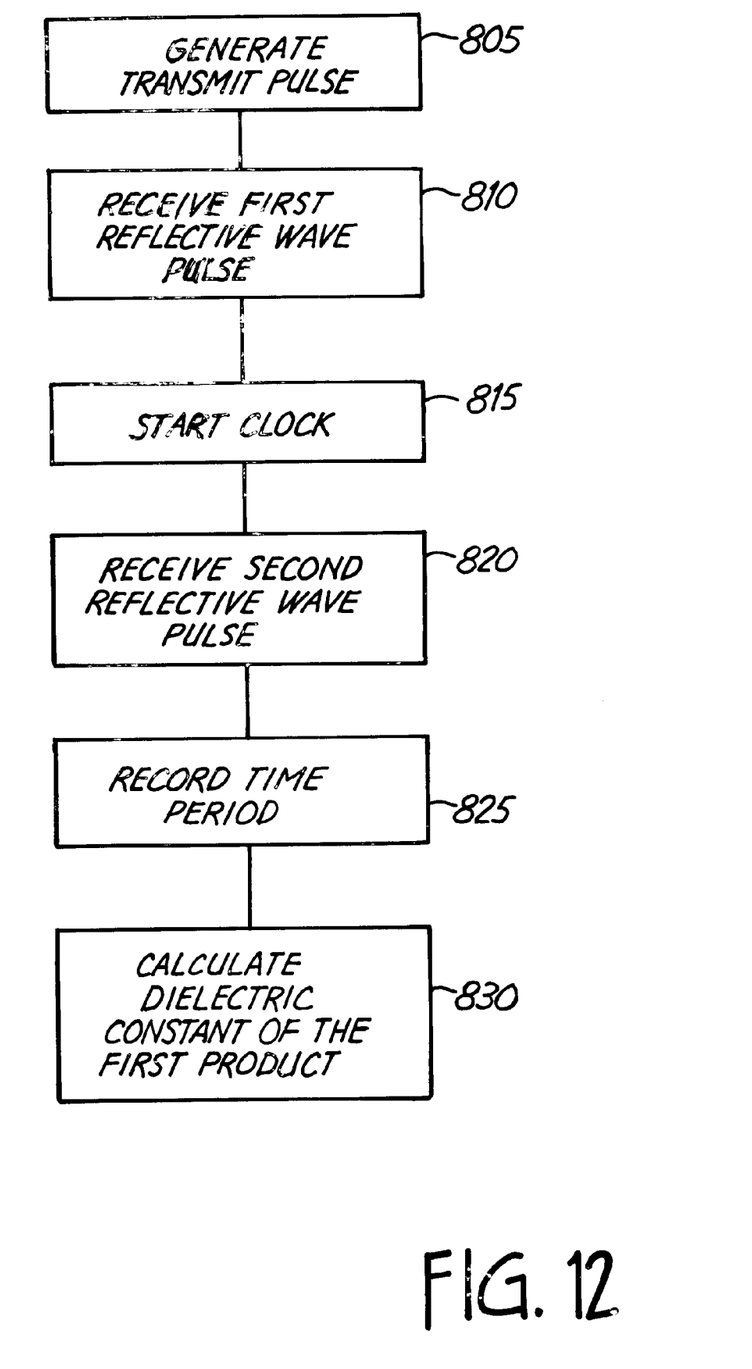

The method begins at block 805 with generation of the transmit pulse. The transmit pulse is transmitted along the termination into products 14 and 15. At block 810, the first reflected wave pulse is received and detected with the threshold controller. Receipt of the first reflected wave pulse starts a clock or designates the beginning of a time period as shown at block 815. Next, the second reflected wave pulse is received and detected at block 820. Receipt of the second reflected wave pulse designates the end of the time period, as shown at block 825 where the time period is recorded. At block 830, the dielectric constant of product 14 is calculated as a function of the recorded time period which is indicative of a time of travel of the microwaves along the termination a known distance through product 14.

Figure 11:
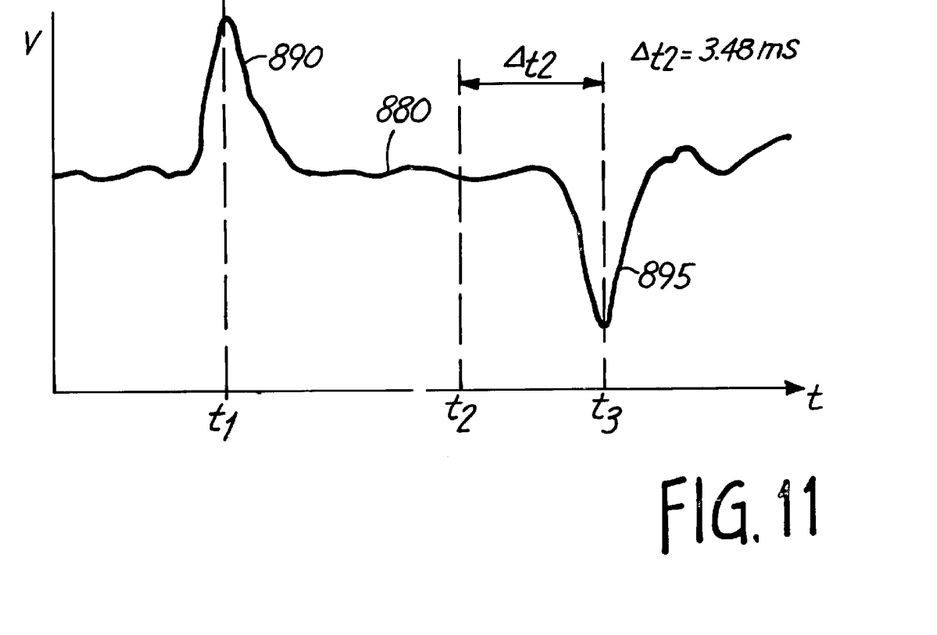

FIGS. 10 and 11 illustrate the method of FIG. 12. FIGS. 10 and 11 illustrate equivalent time LPTDRR waveforms 850 and 880 corresponding to representations of first and second products filling different tanks, with the first and second products having first and second dielectric constants, respectively. In both plots, the product either substantially completely covers the leads of termination 110, or covers them by a known distance.

As can be seen in FIGS. 10 and 11, the time delay between the transmitted pulses (represented by fiducial pulses 860 and 890) and the reflected pulses 870 and 895 (corresponding for example to reflections off of the bottom of tank 12 or termination 110 or to reflections at a product-to-product interface) varies from one material to the next. This variation is due to the different dielectric constants of the materials. This is further illustrated by time differences $\Delta_{t1}$ and $\Delta_{t2}$, which represent the time required for microwaves to travel the same sample distance in each of the two materials. In the material having the first dielectric constant, the time required to travel the sample distance was 3.08 ms, while in the material having the second dielectric constant, the time required to travel the same sample distance was 3.48 ms. Thus, the time delay between transmission of the microwave signal and the reflection off of an interface a known distance down the termination can be used to calculate the dielectric constant.

Although the present invention has been described with reference to preferred embodiments, workers skilled in the art will recognize that changes may be made in form and detail without departing from the spirit and scope of the invention. For example, the above described methods of calculating dielectric constants can be combined to aid in calculating multiple dielectric constants, or to provide a more accurate calculation of dielectric constants.

What is claimed is:

1. A low power radar level transmitter for measuring a dielectric constant of a process product having first and second product interfaces, the transmitter comprising:
    a termination extendable into the process product;
    a pulse generator coupled to the termination, the pulse generator adapted to generate a microwave transmit pulse which is transmitted along the termination into the product, a first portion of the transmit pulse being reflected at a first product interface and a second portion of the transmit pulse being reflected at a second product interface;
    a pulse receiver coupled to the termination and adapted to receive a first reflected wave pulse corresponding to reflection of the first portion of the transmit pulse at the first product interface, and receiving a second reflected wave pulse corresponding to reflection of the second portion of the transmit pulse at the second product interface;
    a threshold controller coupled to the pulse receiver and adapted to detect whether the first reflected wave pulse at least meets a first threshold value and to provide receive pulse output information based upon detection of the first reflected wave pulse;
    a dielectric constant calculator coupled to the threshold controller; and
    wherein the threshold controller is further adapted to detect whether the second reflected wave pulse at least meets a second threshold value, the threshold controller providing the receive pulse output information based upon detection of the first and second reflected wave pulses.

2. The transmitter of claim 1, wherein the second product interface is positioned a known distance along a length of the termination, the receive pulse output information being indicative of a time of travel of the transmit pulse a known distance through the product.

3. The transmitter of claim 1, and further comprising an analog-to-digital converter coupled to the pulse receiver and adapted to digitize the first and second reflected wave pulses, wherein the threshold controller and the dielectric constant calculator comprise a microprocessor coupled to the analog-to-digital converter that is adapted to detect the digitized first and second reflected wave pulses determine the dielectric constant of the product.

4. The transmitter of claim 1, wherein the threshold controller comprises:
    a comparator having first and second inputs, the first input being coupled to the pulse receiver and receiving the first and second reflected wave pulses;
    a microprocessor generating a digital output representative of a desired threshold; and
    a digital-to-analog converter coupled to the microprocessor and receiving the digital output, the digital-to-analog converter converting the digital output to an analog threshold voltage and providing the analog threshold voltage to the second comparator input.

5. The transmitter of claim 1, wherein the termination is a twin lead antenna.

6. The transmitter of claim 1, wherein the transmitter is couplable to a two-wire process control loop, the transmitter further comprising output circuitry couplable to the two-wire process control loop for transmitting information related to the product over the loop.

7. The transmitter of claim 6, wherein the transmitter further comprises power supply circuitry couplable to the two-wire process control loop for receiving power from the loop to provide the sole source of power for the transmitter.

8. The transmitter of claim 7, wherein the process control loop is a 4–20 mA process control loop that operates in accordance with a process industry standard communications protocol.

9. A low power radar level transmitter adapted to measure a dielectric constant of a process product having first and second product interfaces, the transmitter comprising:
    low power time domain reflectometry radar (LPTDRR) circuitry;
    means for controlling the LPTDRR circuitry to calculate a time of travel of microwaves through a known distance of the product which is proportional to the dielectric constant of the product; and
    means for calculating the dielectric constant of the product as a function of the time of travel.

10. A method of using a low power radar level transmitter to measure a dielectric constant of a process product having first and second product interfaces, the method comprising:
    controlling low power time domain reflectometry radar (LPTDRR) circuitry in the transmitter to direct microwave energy into the process product;
    controlling LPTDRR circuitry to receive reflected microwave energy from the process product;
    controlling LPTDRR circuitry to calculate a parameter based upon reception of the microwave energy which parameter is proportional to the dielectric constant of the product;
    calculating the dielectric constant of the product as a function of the calculated parameter; and
    wherein the parameter is a time delay between transmission of microwave energy down a termination extending into the product and reflection of the microwave energy.

11. The method of claim 10, wherein controlling the LPTDRR circuitry to calculate the parameter further includes calculating the time delay between transmission of the microwave energy along the termination and reflection of the microwave energy from a surface.

12. The method of claim 11, wherein the surface is a bottom of a tank containing the process product.

13. The method of claim 11, wherein the surface is a surface of the product a known distance along a length of the termination.

14. The method of claim 11, wherein calculating the dielectric constant of the product as a function of the calculated time delay comprises calculating the dielectric constant of the product as a function of the square of the calculated time delay.

* * * * *

UNITED STATES PATENT AND TRADEMARK OFFICE
CERTIFICATE OF CORRECTION

PATENT NO.    : 6,477,474 B2                                                         Page 1 of 1
DATED         : November 5, 2002
INVENTOR(S)   : Diede It is certified that error appears in the above-identified patent and that said Letters Patent is hereby corrected as shown below:

Title page,
Item [56], References Cited, U.S. PATENT DOCUMENTS, add:
-- 3,474,337   *  10/1969  Petrick ................................... 324/58.5
   6,121,780  *   9/2000  Cruickshank et al. ...................... 324/643 --

FOREIGN PATENT DOCUMENTS, add:
       -- SU    697940A      03/1997
          JP    09069731A    03/1997 --

OTHER PUBLICATIONS, add:

"Micropower Impulse Radar Technology and Application" by, Mast et al., U.S. Dept. of Energy, Lawrence Livermore National Laboratory, UCRL-ID 130474, April 15, 1998.
"Radar Level Technology Offers Accurate, Noncontact Measurements" by, Fred Fitch, Special Report Flow, Level, Pressure, I&CS, January 1996, pp. 27-30.
"Novel Methods of Measuring Impurity Levels in Liquid Tanks", IEEE MTT-S International Microwave Symposium Digest, US, New York, IEEE, pages 1651-1654 (1997)
"Gauging and Level Measurement for Liquids, Interface and Granular Materials", Reflex-Radar, KROHNE, Technical Data BM 100, BM 100 EEx (12/96).
"Eclipse Guided Wave Radar", Magnetrol, pages 1-2 (July 23, 1998).
"Approval Standard Intrinsically Safe Apparatus and Associated Apparatus for use in Class I, II and III, Division 1 Hazardous (Classified) Locations", Factory Mutual Research, Class No. 3610, pages 1-32 (October 1988).
"Measuring Fluid Levels with Radar", by Steven Ashley, Mechanical Engineering, pages 82-83 (January 1996).
"World's Fastest Solid-State Digitizer", Lawrence Livermore National Laboratory, Energy & Technology Review, pages S1-S6 (April 1994).
"Low-Cost Wideband Spread-Spectrum Device Promises to Revoluionize Radar Proximity Sensors", Technology Advances, Electronic Design (July 25, 1994).

Signed and Sealed this

Twenty-ninth Day of April, 2003

JAMES E. ROGAN
*Director of the United States Patent and Trademark Office*